United States Patent
Gupta et al.

(10) Patent No.: US 10,969,388 B2
(45) Date of Patent: Apr. 6, 2021

(54) ASSAY AND KIT FOR DETECTION OF ENDOTOXIN

(71) Applicant: NanoDx Healthcare Pvt. Ltd., New Delhi (IN)

(72) Inventors: Shalini Gupta, New Delhi (IN); Venkataraman Sritharan, Telangana (IN); Prasanta Kalita, New Delhi (IN)

(73) Assignee: NanoDx Healthcare Pvt. Ltd., New Delhi (IN)

( * ) Notice: Subject to any disclaimer, the term of this patent is extended or adjusted under 35 U.S.C. 154(b) by 163 days.

(21) Appl. No.: 16/082,754

(22) PCT Filed: Nov. 11, 2016

(86) PCT No.: PCT/IN2016/050397
§ 371 (c)(1),
(2) Date: Sep. 6, 2018

(87) PCT Pub. No.: WO2017/154013
PCT Pub. Date: Sep. 14, 2017

(65) Prior Publication Data
US 2019/0079088 A1   Mar. 14, 2019

(30) Foreign Application Priority Data

Mar. 7, 2016 (IN) .............................. 201611007932

(51) Int. Cl.
| | | |
|---|---|---|
| *G01N 33/569* | (2006.01) | |
| *G01N 33/543* | (2006.01) | |
| *G01N 33/531* | (2006.01) | |
| *G01N 33/58* | (2006.01) | |

(52) U.S. Cl.
CPC ..... *G01N 33/56911* (2013.01); *G01N 33/531* (2013.01); *G01N 33/543* (2013.01); *G01N 33/54366* (2013.01); *G01N 33/587* (2013.01); *G01N 2400/50* (2013.01)

(58) Field of Classification Search
None
See application file for complete search history.

(56) References Cited

U.S. PATENT DOCUMENTS 5,510,242 A   4/1996   Blais

FOREIGN PATENT DOCUMENTS

| WO | 2005/003163 | 1/2005 |
| WO | 2010/021872 | 2/2010 |
| WO | 2014/014890 | 1/2014 |

OTHER PUBLICATIONS

Yu et al. J. Microbiological Methods 68: 277-282, 2011.*
Kalita, P. et al. "Nanoparticle-Drug Bioconjugate as Dual Functional Affinity Ligand for Rapid Point-of-Care Detection of Endotoxin in Water and Serum", Analytical Chemistry, 2015, vol. 87, No. 21, pp. 11007-11012.
Jagtap, P. et al. "A Flowthrough Assay for Rapid Bedside Stratification of Bloodstream Bacterial Infection in Critically Ill Patients: a Pilot Study", Journal of Clinical Microbiology, vol. 56, issue 9, Sep. 2018, pp. 1-13.
International Search Report and Written Opinion dated Mar. 2, 2017, from International Application No. PCT/IN2016/050397, 12 pages.

\* cited by examiner

*Primary Examiner* — Sarvamangala Devi
(74) *Attorney, Agent, or Firm* — Meunier Carlin & Curfman LLC

(57) ABSTRACT

The present invention relates to a membrane based assay method, device and kit for rapid detection and/or quantification of endotoxins in aqueous solutions and test samples. The kit as per the present invention comprises lipopolysaccharide (LPS) affinity ligand conjugated with gold nanoparticles (GNPs); a membrane device comprising an endotoxin affinity membrane positioned parallelly to one or more layer(s) of a hydrophilic material, which are optionally secured in an enclosure; and optionally comprising an indicator chart for quantification of endotoxins in the sample. The method comprises placing the sample suspected of endotoxin contamination on a surface of a membrane comprised in a membrane device; placing once or more a suspension of LPS-affinity ligand conjugated with GNPs over the same area as the sample placed and detecting the presence of endotoxin if the colour signal appears and based on its intensity quantifying the endotoxin levels.

12 Claims, 9 Drawing Sheets
Specification includes a Sequence Listing.

| Colour | Symbol |
|---|---|
|  | ++++ |
|  | +++ |
|  | ++ |
|  | + |
|  | ± |

FIG. 4

ASSAY AND KIT FOR DETECTION OF ENDOTOXIN

FIELD OF THE INVENTION

The present invention relates to an assay, a device and a kit for detection of endotoxin in a sample. More particularly, the present invention relates to a membrane based assay method, device and kit for rapid endotoxin detection in a sample.

BACKGROUND OF THE INVENTION

Endotoxin detection in test samples from pharmaceutical and food industries as well as in clinical and healthcare setup is of paramount importance. Exposure to endotoxins associated with Gram-negative bacteria (GNB) can lead to effects such as fever, cytokine system activation, endothelial cell destruction, blood vessel permeability, or other adverse effects. Endotoxin or lipopolysaccharide (LPS) present on the cell wall of GNB is responsible for many toxic effects that occur during GNB sepsis and plays an important role in the pathophysiology of such infections.

All parenteral and biological pharmaceutical products and processed food items require rapid pyrogen testing for safety an quality assurance as otherwise, the presence of endotoxin in injectable and oral formulations and food products can lead to inflammatory reactions and septic shock in patients. GNB endotoxin being one of the most ubiquitous pyrogens likely to be found in any manufacturing environment calls for a rapid endotoxin testing method and detection device that can be integrated with any large-scale pharmaceutical, biologics and food production unit. Moreover, improper storage conditions of food items can lead to growth of contaminant bacteria that produce toxins. To monitor the quality of the food products, it is necessary to perform endotoxin testing from time to time for health and safety.

Also, operation theatres, fermentation units and biological laboratories require autoclaved utensils and tools and regularly require using endotoxin-free grade water. Sterilization of devices and solutions using a heating method can kill GNB that might be present in the product or solution with the release of endotoxin that can remain in the product. The endotoxin can be heat stable and hence, tools, solutions and water to be used in such settings needs to be tested for endotoxin levels.

Further, endotoxins are a significant concern in the field of nephrology where patients receive dialysis, which provides life-saving renal replacement for end-stage renal disease. As the occurrence of endotoxin-mediated pyrogenic reactions continues to occur in those individuals receiving dialysis, water for dialysis as well as dialysates need be sterile and ensured to have bacterial endotoxins absent or within permissible limits. It has been recommended that each dialysis center develop microbiological and endotoxin surveillance policies and procedures for the testing of hemodialysis fluids such as water and dialysate solutions.

Moreover, sepsis is the single largest cause of hospital-acquired infections and fatalities especially in resource-poor settings. Despite advances in antimicrobial therapy, septic shock and other clinical complications due to GNB infections continue to pose a major health problem. Exposure to endotoxins associated with GNB plays an important role in the pathophysiology of these infections. Endotoxins mediate toxicity and release of factors like tumor necrosis factor and interleukins besides forming a rigid shield around the bacteria protecting them from the effects of antibiotics. The delay in initiation and/or ineffectiveness of appropriate antibiotic therapies can lead to fatalities. Commonly applied sepsis detection methods based on microbiological analysis are hampered by the uncertainties associated with the growth of bacterial pathogens in culture media due to prior antibiotic exposure, while newer methods based on detection of procalcitonin (PCT) levels, a surrogate sepsis biomarker, in serum are unable to offer definitive results. Recent studies indicate that endotoxins, the highly conserved cell wall components of GNB, can serve as an early and pathogen-specific biomarker for sepsis diagnosis. Endotoxin levels in serum rise well within 2 hours, while PCT levels take nearly 2 to 6 hours, thereby uniquely positioning endotoxins as an early biomarker for sepsis diagnosis. The diagnosis of systemic infection/sepsis at the pre-symptomatic stage of infection can allow early administration of effective therapeutics and dramatically reduce mortality and morbidity.

Initially for many years, bacterial endotoxin tests (BETs) were performed by the USP Rabbit Pyrogen Test, a time-consuming and costly animal test. Subsequently, the Limulus Amebocyte Lysate (LAL) test became a standard in-vitro test for Gram-negative endotoxin detection. LAL test and its many versions are time consuming and need expensive equipments like incubators (heating and heat control unit), photometers, a special machine to detect the test results, e.g., a microplate reader, etc. These methods need specialized technical expertise, are required to be performed inside a laboratory and require expensive equipments increasing the cost per test.

From the foregoing it is apparent that there is a need in the art for a test kit and method for a rapid, simple, and cost-effective detection of endotoxins in aqueous solutions and test samples that be integrated in any industrial or clinical set-up.

SUMMARY OF THE INVENTION

Accordingly, the present invention in general aspects provides a membrane based assay method, device and kit for rapid detection of endotoxins in a sample.

In one embodiment, the present invention provides a membrane based assay method for detection of endotoxins in a sample, the method comprising:
  i) placing the sample suspected of containing endotoxin on a surface of a membrane having affinity to endotoxin positioned parallelly to at least one layer of a hydrophilic material and optionally placed in an enclosure for securing therein the layer(s) of hydrophilic material and the membrane having affinity to endotoxin positioned thereon;
  ii) placing at least once a suspension of conjugates of LPS-affinity ligand with gold nanoparticles (GNPs) over the same area as the sample placed; and
  iii) detecting and/or quantifying the endotoxin in the sample based on the appearance of the colour signal.

In an embodiment, the membrane based assay method for detection of endotoxins as per the present invention optionally comprises a step of adding a protein solution following the placement of the sample over the same area for minimizing any non-specific binding in the subsequent steps.

In another embodiment, the membrane based assay method for detection of endotoxins as per the present invention optionally comprises placing the suspension of conjugates of LPS-affinity ligand with GNPs more than once until the intensity of the coloured signal saturates; and comparing the saturated coloured signal against an indicator chart to determine the endotoxin concentration in the sample.

In one embodiment, the membrane based assay method for detection of endotoxins as per the present invention optionally comprises adding ultrapure water free of endotoxins over the coloured signal appeared subsequent to the placement of the suspension of conjugates of LPS-affinity ligand with GNPs for removing any excess unbound GNPs and improving the accuracy of determination of endotoxin levels in the sample.

In one embodiment, the sample suspected of containing endotoxins is selected from the group consisting of liquid sample, industrial sample, pharmaceutical industry and product sample, veterinary industry and product sample, food sample, environmental sample, and optionally a biological sample.

In an embodiment, the present invention provides a membrane device to be adopted for detection of endotoxins in a sample comprising:
a) a membrane having affinity to endotoxin;
b) at least one layer of a hydrophilic material positioned parallelly to the membrane having affinity to endotoxin; and
c) an enclosure for securing therein the layer(s) of hydrophilic material and the membrane having affinity to endotoxin positioned thereon.

In one embodiment, the present invention provides a kit for detection of endotoxins in a sample comprising of:
i) LPS-affinity ligand conjugated with GNPs; and
ii) a membrane device comprising:
a) a membrane having affinity to endotoxin;
b) at least one layer of a hydrophilic material positioned parallelly to the membrane having affinity to endotoxin; and
c) an enclosure for securing therein the layer(s) of hydrophilic material and the membrane having affinity to endotoxin positioned thereon.

In one embodiment, the kit for detection of endotoxins optionally comprises an indicator chart for quantitative determination of endotoxin concentrations in the sample.

The details of one or more aspects set forth in the accompanying drawings not necessarily drawn to scale are incorporated in and constitute a part of this application. They illustrate some of the embodiments of the present invention together with the description below. Other features, objects, and advantages will be apparent from the description and drawings, and from the claims.

BRIEF DESCRIPTION OF THE DRAWINGS

FIG. 1.

Figure 4:
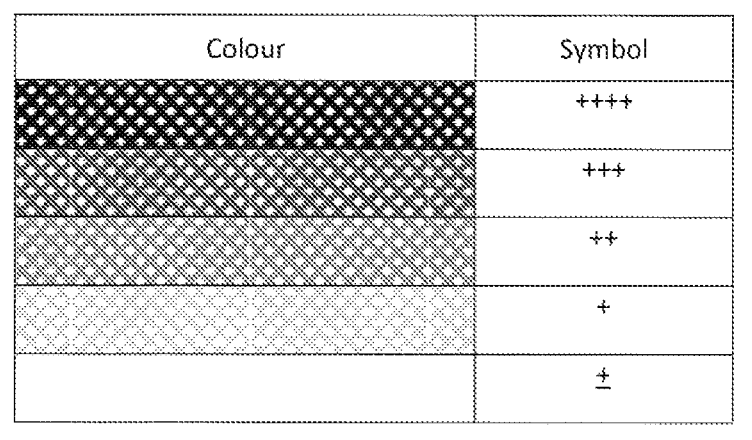

FIG. 4 shows an indicator chart to determine the endotoxin concentration in the sample as per one of the embodiments of the invention.

FIG. 5.

FIG. 6.

FIG. 7.

DETAILED DESCRIPTION OF THE INVENTION

Figure 1A:
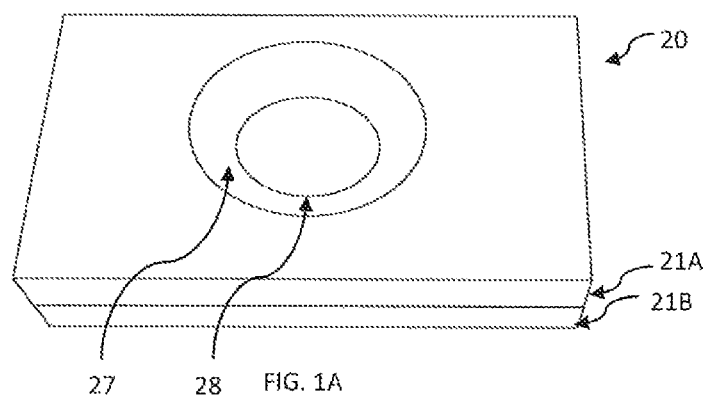
FIG. 1A is a schematic representation of an enclosure component of a membrane device according to one of the embodiments of the present invention and FIG. 1B is a schematic representation of the membrane having affinity to endotoxin positioned parallelly to plurality of layers of a hydrophilic material according to one embodiment of the present invention.

The term "Endotoxin" or "Endotoxins" includes or means or may be used interchangeably with terms "lipopolysaccharides" or "LPS" as may be known to a person skilled in the art that lipopolysaccharides are endotoxins.

The term "membrane based assay" as used herein refers to an assay format which employs a membrane during the assay for example, the membrane having affinity to endotoxins or membranes which are hydrophilic. The term "membrane based assay" also includes assay formats such as flow through assay, lateral flow assay or any other format employing membranes for carrying out the assay.

The term "membrane device" as used herein refers to a device that primarily comprises of membranes of different types for example, one type of membrane includes membranes having affinity to endotoxins and other type of membranes are those which are made of hydrophilic material having absorbing ability to allow the liquid sample, test solutions and other reagents to flow through it rapidly.

The term "conjugates of LPS-affinity ligand with gold nanoparticles (GNPs)" as used herein refers to GNPs conjugated with a ligand having affinity to lipopolysaccharides or endotoxins.

The term "fluid communication" as used herein refers to flow or communication of fluid or liquid through or across membranes that is membrane having affinity to endotoxins and hydrophilic membrane.

As used herein the term "multilayers" is used interchangeably with the term "plurality of layers" and refers to layers made of hydrophilic material.

The present invention relates to a membrane based assay method, device and kit for rapid, simple, and cost-effective detection of endotoxins in aqueous solutions and test samples that can be integrated in any industrial or clinical set-up.

The membrane based assay method can be embodied in a flow through format or can be adopted in a lateral flow assay.

In some of the embodiments, the present invention provides a membrane based assay, device and kit to be adopted in a flow through format for rapid, simple, and cost-effective detection of endotoxins in a sample.

In one embodiment, the present invention provides a membrane based assay method for detection of endotoxins in a sample, the method comprising:
  i) placing the sample suspected of containing endotoxin on a surface of a membrane having affinity to endotoxin positioned parallelly to at least one layer of a hydrophilic material and optionally placed in an enclosure for securing therein the layer(s) of hydrophilic material and the membrane having affinity to endotoxin positioned thereon;
  ii) placing at least once a suspension of conjugates of LPS-affinity ligand with GNPs over the same area as the sample placed; and
  iii) detecting and/or quantifying the endotoxin in the sample based on the appearance of the colour signal.

In one embodiment, the sample suspected of containing the endotoxins is selected from the group consisting of water sample, liquid sample, industrial sample, pharmaceutical sample, veterinary product sample, food sample, environmental sample, or optionally a biological sample.

In one embodiment, the sample is a liquid sample, such as water or other agents used or a sample of process stream produced in pharmaceutical, veterinary or food industry; research or clinical laboratories or hospitals.

The industry sample includes sample from any industry suspected of contamination with endotoxins.

The pharmaceutical industry and product sample includes sample of pharmaceutical industry process stream, intermediate as well as product which may be for any mode of administration for parenteral, oral or local.

The veterinary industry and product sample includes sample of veterinary industry process stream, intermediate as well as product for animals.

The food sample includes sample of any food preparation, nutraceutical, health supplement or functional food product.

The environmental sample includes, but not limited to, water, rain samples, soil, mud, minerals, fluid, waste, washing of tools, or the ones obtained from a surface, for example, of operation theatres of intensive care units in a hospital or clinical or research set-up requiring sterile atmosphere, a device used in a hospital, clinical or laboratory setting and analyzed for the absence of GNB or endotoxins.

The sample is optionally a biological sample. The biological fluid includes a cell culture medium or supernatant of cultured cells. Alternately, the biological sample is a sample of subject such as human or animal and includes, but is not limited to, any biological fluid, including a bodily fluid. Examples of bodily fluids include, but are not limited to, plasma, serum, whole blood, saliva, urine, tissue infiltrate, pleural effusions, lung lavage fluid, and the like. The use of such biological sample in the membrane based assay method of the present invention allows monitoring the onset and extent of bacterial infection in blood samples as well as to determine the response of a subject to antibiotic therapy or to carry out in-vitro testing in drug discovery to determine the response of the drug to a bacterial disease caused by endotoxin.

The sample to be used is optionally made free of micron-sized components that can clog the membrane during the assay. The sample as required may be diluted sufficiently prior to the assay.

In an embodiment, the membrane based assay method for detection of endotoxin as per the present invention optionally comprises a step of adding a protein solution following the placement of the sample over the endotoxin affinity membrane for minimizing any non-specific binding in the subsequent steps of addition of the suspension of LPS-affinity ligand with GNPs. The protein solution is for example bovine serum albumin.

In another embodiment, the membrane based assay method for detection of endotoxin as per the present invention comprises placing of the suspension of LPS-affinity ligand with GNPs more than once until the intensity of the colour signal does not change.

In one embodiment, the membrane based assay method for detection of endotoxin as per the present invention optionally comprises adding ultrapure water free of endotoxins over the colour signal appearing subsequent to placing of the suspension of conjugates of LPS-affinity ligand with GNPs, for removing any excess particles and thereby improving the accuracy of determination of endotoxin levels in the sample.

In one embodiment, the membrane based assay method includes step of comparing the intensity of the colour signal appeared against an indicator chart to determine the endotoxin concentration in the sample for quantitative assays.

In case of the sample containing endotoxins, the colour signal as a result of the membrane based assay method of the present invention appears rapidly once the suspension of conjugates of LPS-affinity ligand with GNPs is placed over the sample spot that is as soon as the ligand part of the conjugates of LPS-affinity ligand with GNPs binds with endotoxins present in the sample which is bound on the surface of membrane and colour of GNPs becomes visible thus producing the colour signal. The colour signal is produced within 3 seconds.

In an embodiment, the present invention provides a membrane device to be adopted for detection of endotoxins in a sample comprising:
  a) a membrane having affinity to endotoxin;
  b) at least one layer of a hydrophilic material positioned parallelly to the membrane having affinity to endotoxin; and
  c) an enclosure for securing therein the layer(s) of hydrophilic material and the membrane having affinity to endotoxin positioned thereon.

The upper layer of membrane having affinity to endotoxin of the membrane device is a membrane that is capable of binding to endotoxins including LPS. The upper layer of membrane having affinity to endotoxin allows rapid passing of the sample through it. The membrane is selected to have a pore size which permits such rapid drawing of the sample. Any of a variety of members may be used including membranes of various synthetic or natural materials.

In one embodiment, the endotoxin affinity membrane of the membrane device is selected from a group consisting of but not limited to: cellulose, nitrocellulose, cellulose ester, nylon, polysulfone, polyether sulfone, polyvinylidene difluoride, polyethylene tetrafluoride, polycarbonate, polyester, polypropylene, polyamide, paper, glass fiber, silica fiber, stainless steel fiber or any other polymeric material to which endotoxins bind.

In one embodiment, the membrane having affinity to endotoxin is selected from the one having pores with a diameter between 0.1 and 12 µm and has a thickness up to 2500 µm. Membranes with pore sizes of 0.1, 0.2, 0.21, 0.22, 0.23, 0.25, 0.26, 0.27, 0.28, 0.29, 0.3, 0.35, 0.4, 0.45, 0.5, 0.55, 0.6, 0.65, 0.7, 0.8, 1, 1.2, 2, 2.5, 3.0, 5.0, 8.0, 10 and 12 µm may be used.

In one embodiment, the membrane having affinity to endotoxin is selected from the one having pores with a diameter between 0.1 and 0.5 µm and a thickness up to 500 µm.

In one embodiment, the membrane device comprises the multilayer of a hydrophilic material positioned parallelly to the membrane having affinity to endotoxin. In one embodiment, the membrane device comprises, parallelly placed below the upper endotoxin affinity membrane, the plurality of layers of absorbent pads made of hydrophilic material for drawing the liquid therethrough.

The absorbent multilayers to be placed below the upper layer of membrane having affinity to endotoxin is made from hydrophilic material having absorbing property, for example the material is selected from cellulose, cellulose acetate, cotton, paper; various dried gels, such as silica gel, agarose, dextran, gelatin; porous polyethylene, polyester, polyolefin, or any other polymeric hydrophilic material having absorbing capacity. Suitable hydrophilic material particularly includes cellulose products. In the exemplary embodiment, the membrane device comprises layers of non-woven absorbent cellulose.

In one embodiment, the plurality of layers of hydrophilic material is a stack of absorbent pads having high wicking capacity. The absorbent pads are such that they increase the speed of the assay by overcoming diffusional mass-transfer limitations and help remove free background molecules that may interfere with the final assay result. In one embodiment the hydrophilic multilayers to be placed below the upper endotoxin affinity membrane are for example absorbent pads of type AP080, AP110, AP120 or any such similar absorbent pad.

The enclosure component of the membrane device for holding the multilayer of the hydrophilic material and the upper endotoxin affinity membrane thereon can be an enclosure of any shape for example square or circle, made of material non-reactive to the solutions and reagents used in the membrane based assay method of the present invention, for example the enclosure is made of glass, plastic or similar polymeric material. The enclosure holding the multilayer of the hydrophilic material and the upper endotoxin affinity membrane is provided with opening from which the sample and other reagents can be placed during the assay.

In one embodiment, the enclosure comprises a lower component in which the multiple layers of the hydrophilic material are placed, over which the upper endotoxin affinity membrane is positioned. The upper component of the enclosure is secured over the lower component for firmly holding the membranes placed therein. The upper component of the enclosure is provided with an opening that leaves a portion of the membrane having affinity to endotoxin exposed on which the sample and reagents would be placed during the assay.

In one embodiment, the enclosure is the cassette made of plastic by injection-molding.

In one embodiment, the present invention provides a kit for detection of endotoxins in a sample comprising:
  i) LPS-affinity ligand conjugated with GNPs; and
  ii) a membrane device comprising:
    a) a membrane having affinity to endotoxin;
    b) at least one layer of a hydrophilic material positioned parallelly to the membrane having affinity to endotoxin; and
    c) are enclosure securing therein the layer(s) of hydrophilic material and the membrane having affinity to endotoxin positioned thereon.

The kit as provided by the present invention is a kit for fast detection of endotoxins in a sample.

In one embodiment the kit for fast detection of endotoxins in a sample when employed detects endotoxin within a few seconds. For example, the components of the kit when employed can detect endotoxins in the sample in less than 90 seconds when the steps as per the assay method as described herein are followed.

The GNPs are covalently conjugated with the LPS-affinity ligand that is ligand having high specific affinity to bacterial endotoxin and function as detection probes in the assay.

In one embodiment the GNPs to be used for forming the conjugates with the LPS-affinity ligand are citrate-stabilized GNPs for example of dimension 1 to 100 nm. The GNPs can be synthesized using a method known in the art for example as disclosed by Slot et al. (J. W. Slot, H. J. Geuze, "A new method of preparing gold probes for multiple labelling cytochemistry," Eur. J. Cell Biol., 38, 87-93, (1985)), Tsai et al. (C. Y. Tsai, D. S. Lee, Y. H. Tsai, B. Chan, T. Y. Luh, P. J. Chen, P. H. Chen, "Shrinking gold nanoparticles: dramatic effect of a cryogenic process on tannic acid/sodium citrate-generated gold nanoparticles," Materials Lett., 58, 2023-2026, (2003)) and Kalita et al. (Kalita P., Dasgupta A., Sritharan V., Gupta S.; "Nanoparticle-drug bioconjugate as dual functional affinity ligand for rapid point-of-care detection of endotoxin in water and serum", Anal. Chem., 87 (21), 11007-11012 (2015)). The size, concentration and stability of the GNPs are characterized using transmission electron microscopy (TEM), UV-visible spectroscopy, dynamic light scattering (SLS) and zeta potential measurements as reported in Kalita et al. The GNPs suspension can be stored at a cold temperature for example below 10° C., preferably around 4° C. for a very long duration of at least 6 months without losing stability.

The LPS-affinity ligand for forming conjugates with GNPs is an antibiotic drug having high specific affinity to bacterial endotoxin, especially endotoxins produced by GNB and functions as detection probe in the assay.

The antibiotic drug used for conjugation with GNPs is elected from the group consisting of polymyxin B (PMB) sulphate, polyamine sulphonamides, alexidine and chlorhexidine which have affinity to bind endotoxins.

In one embodiment, the antibiotic drug is PMB.

In one embodiment, the LPS-affinity ligand for forming conjugates with GNPs includes the protein antibodies and peptide molecules that have affinity and bind to endotoxins.

In one embodiment, the LPS-affinity ligand is a protein peptide for example sushi peptide. The sushi peptide is a synthetic peptide selected from the group consisting of: sushi 1 peptide; sushi 3 peptide; sushi 4 peptide; sushi 5 peptide; sushi 6vg1 peptide; sushi-7-vg2 peptide; sushi-8-vg3 peptide; and sushi-9-vg4 peptide.

The LPS-affinity ligand conjugated GNPs are formed by any method known in the art. For example the PMB conjugated GNPs are prepared and optimized by following the protocol as reported by Kalita et al (Kalita P., Dasgupta A., Sritharan V., Gupta S.; "Nanoparticle-drug bioconjugate as dual functional affinity ligand for rapid point-of-care detection of endotoxin in water and serum", Anal. Chem., 87 (21), 11007-11012 (2015)).

Alternately, any other chemistry such as using EDC/NHS say may also be suitably applied depending on the type of drug and the surface capping ligand present on the GNPs.

The conjugates of PMB or any other drug or ligand having affinity to LPS conjugated with GNPs are required to contain at least one drug or ligand molecule on the surface of each GNP, for example each GNP on an average comprise around 10 to 20 LPS-affinity ligand or drug molecules on its surface.

The sushi peptide conjugated GNPs may be prepared by a method herein described below by adding the peptide solutions to GNP suspension in a specific relative molar ratio and incubated for sufficient time for forming the covalent conjugates. The molar ratio in which the GNPs and sushi peptides are mixed may be 1:1000, 1:2500, 1:5000, 1:7500, 1:10000, and 1:15000, preferably a ratio below 1:10000 (GNP:sushi peptide), more preferable is a ratio below 1:5000.

In an embodiment, the kit for detection of endotoxins optionally comprises an indicator chart for determination of endotoxin concentrations in the sample, for example the indicator chart is a concentration-calibrated colour chart for easy visualization and scoring of endotoxin levels in the sample thereby quantifying the endotoxins present in the sample.

In one embodiment, the indicator chart is a concentration calibrated colour chart for easy visualization and marked with scoring for quantifying from about >10 ng/mL of endotoxin level to about <100 pg/mL of endotoxin level in the sample.

In an embodiment, the kit for detection of endotoxins optionally comprises a protein solution, endotoxin free water, other reagent(s), device(s), container(s), injector(s), applicator(s), dropper(s) and an insert with instructions for employing the kit to detect endotoxins in the sample.

The kit for detection of endotoxins optionally comprises a protein solution, buffer(s), wash reagent(s), endotoxin free water or any other reagent(s).

In one embodiment, the kit comprises bovine serum albumin.

The kit for detection of endotoxins optionally includes other device(s), container(s), liquid dispenser bottle(s), injector(s), applicator(s), or droppers to be used while carrying out the membrane based assay method and instructions for employing the kit to detect endotoxins in the sample.

One of the optionally included devices in the kit for detection of endotoxin may be a device for separating plasma from a blood sample.

The kit can also be designed to be disposable and for single use to minimize effects of secondary contamination.

The present invention membrane based assay method, device and kit allows rapid detection of bacterial endotoxin in a sample within minutes as against the currently used other kits and assays in the art requiring long hours. The device and kit are portable, and hence allow the integration of membrane device and assay in any industrial, clinical or research setting and can be used at home and even in field for quick endotoxin detection in a given sample as well as for high throughput screening. The membrane device and components of the kit are preferably disposable making it very cost effective. The use of an antibiotic drug in drug conjugated GNPs makes the device, kit and method manifold cheaper than antibody-based diagnostic approaches, also the drug is more thermostable than the antibody, hence making the method more rugged.

The membrane device, kit and assay of the present invention not only allows quick detection of endotoxin in sample but also produces colorimetric signal in the ng/mL to lower pg/mL range that can be observed by the bare eye, thus allowing determination of minute quantities of endotoxin in the sample. Moreover, no ancillary equipment is required for signal detection. Thus, the device, kit and assay can be used right by a patient's bedside helping to curtail reliance on physical symptoms and empirical treatment leading to lowering of overall cost of therapy and antibiotic drug resistance. The assay is very easy to perform, requires minimal technical intervention, lacks any sample preparation or complicated steps and hence, can be run equally well by a skilled or non-skilled worker in both urban and rural settings alike.

The present invention fulfils the requirement of an urgent and unmet need for a fast, reliable and cost-effective method for detection of endotoxin in a sample by very simple and easy to use device, kit and assay.

All of these embodiments of the present invention are based on experimental evidence as described in the example section. The following examples are put forth to illustrate the exemplary embodiments of the invention relating to articles, devices, kit and/or methods. The examples are not to be considered limiting the scope of the invention, which is defined only by the claims following.

EXAMPLE

Example 1

Figure 1B:
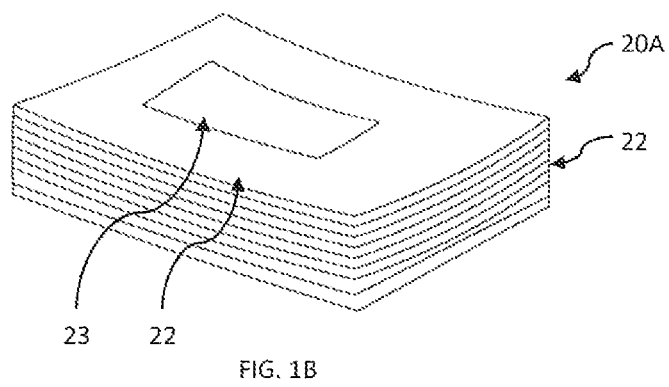
Figure 2:
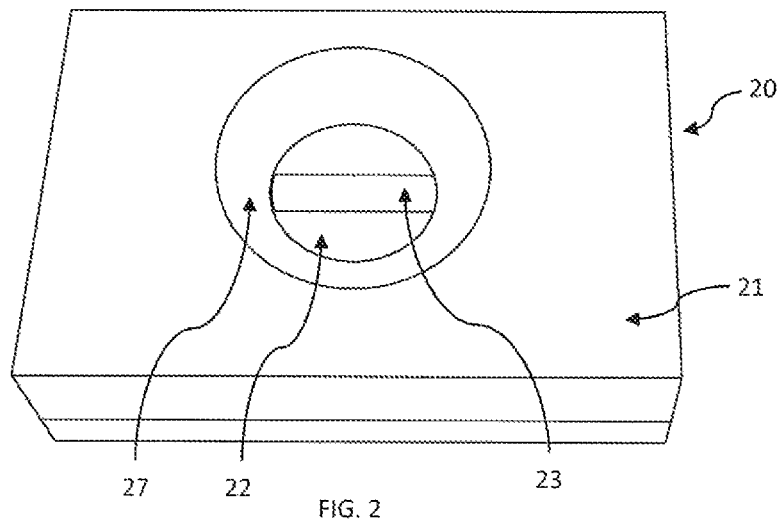
FIG. 2 is a schematic representation of a membrane device according to one embodiment of the present invention.

Membrane Device:

Plastic cassette 21 (FIG. 1A) of 4 cm×3 cm×1 cm dimension made by injection-molding having an upper component 21A and lower component 21B and was used as an enclosure for enclosing membranes therein. As shown in FIG. 2, in the lower component 21B multiple layers of membranes 20A as shown in FIG. 1B were placed. The multiple layers of membranes 20A included a stack of high wicking capacity absorbent pads 22 type-AP080 (Advanced Microdevice Pvt. Ltd. Amabala, India), over which was placed an endotoxin-affinity membrane 23 of nitrocellulose type-SCNM; pore size 0.22 µm; (Advanced microdevice Pvt. Ltd., Amabala, India). The upper component 21A is provided with an opening 28 created by the concave depression 27 which firmly holds the membranes in the component 21B. The opening 28 allows placing of the sample and other reagents through it over the endotoxin-affinity membrane 23. The membrane device 20 when constructed appeared as seen in FIG. 2.

Example 2

Synthesis of Citrate-Stabilized GNPs:

Citrate-stabilized GNPs of size 16±4 nm were synthesized by following the method as reported in the literature mentioned hereinabove in the detailed description.

Briefly, $HAuCl_4 \cdot 3H_2O$ was reduced with an aqueous solution of sodium citrate and tannic acid. 10 mL of 1% (w/v) $HAuCl_4$ solution was diluted to 800 ml with uitrapure DI water (solution A) and another aqueous solution containing 40 mL of 1% (w/v) sodium citrate and 100 µL of 0.1% (w/v) tannic acid was diluted to 200 mL (solution B), Both A and B solutions were mixed at 60° C. and kept for 4 h under constant stirring. The mixture changed its colour from light yellowish to black to violet and finally to red. The mixture was removed from heat and immediately chilled in an ice bath to quench the reaction. The prepared AuNP suspension was then stored at 4° C. until further use. The stability of the AuNP suspension was checked for 3 consecutive months by UV-Visible spectroscopy and found to be stable. The size of the NPs was determined using transmission electron microscopy (TEM), UV-visible spectroscopy and dynamic light scattering (DLS).

Example 3

Preparation of Polymyxin B (PMB) Sulfate Antibiotic Drug Conjugated GNPs:

Polymyxin B (PMB) sulfate antibiotic drug conjugated GNPs were prepared by the protocol as reported by Kalita et al as follows:

The covalent conjugation of PMB to GNPs was performed in three steps. 10 mL of 18 nM aqueous GNPs suspension was incubated at room temperature with 100 µL, of 18 mM DTH in ethanol for 8 h under constant stirring at 50 rpm using rotospin. This allowed the DTH to ligand place exchange with the surface-capping citrate groups on gold. Excess DTH was removed by centrifuging three times at 5080, 7040 and 17540 rcf (g force), respectively, for 15 min each and the particles were resuspended in 20 mL of 2.5% v/v GLA in HEPES buffer. The suspension was left for incubation at room temperature overnight under constant stirring at 50 rpm using rotospin. The amine reactive conjugates obtained at this stage were washed thrice by centrifugation as described above and the NP pellet was resuspended in 8 ml of 20 nM PMB solution in HEPES buffer. After 16 h of incubation at room temperature under constant stirring at 50 rpm using rotospin, the unconjugated PMB molecules were removed by three times centrifugation as described above. The unreacted aldehyde groups were passivated by incubating with 1 mL of 20 mM glycine at room temperature for 30 min to minimize any nonspecific interactions in the subsequent stages. Finally, the GNP-PMB conjugates were centrifuged thrice as described above, resuspended in 6 mL of HEPES buffer and stored at 4° C. until further use. Each particle on average contained 10 drug molecules on its surface. The particles remained stable up to at least 6 weeks.

Example 4

Blood to Plasma Separation:

A small portable device (RPSD-150/RPSD-450, Advanced Microdevice Pvt. Ltd., Amabala, India) (drawing not shown) was used to separate out the plasma from human blood. Approx. 200 µL of LPS spiked blood was put into the device and the plasma was collected after filtration. To ensure that there was little loss of endotoxins during the filtration process, whole blood was spiked with LPS of known concentrations and then the plasma obtained after filtration and the endotoxin levels were compared with the help of the colour chart. Based on the results, it was concluded that the filtration process did not have any significant effect on the concentration levels of endotoxin.

Example 5

Figure 3:
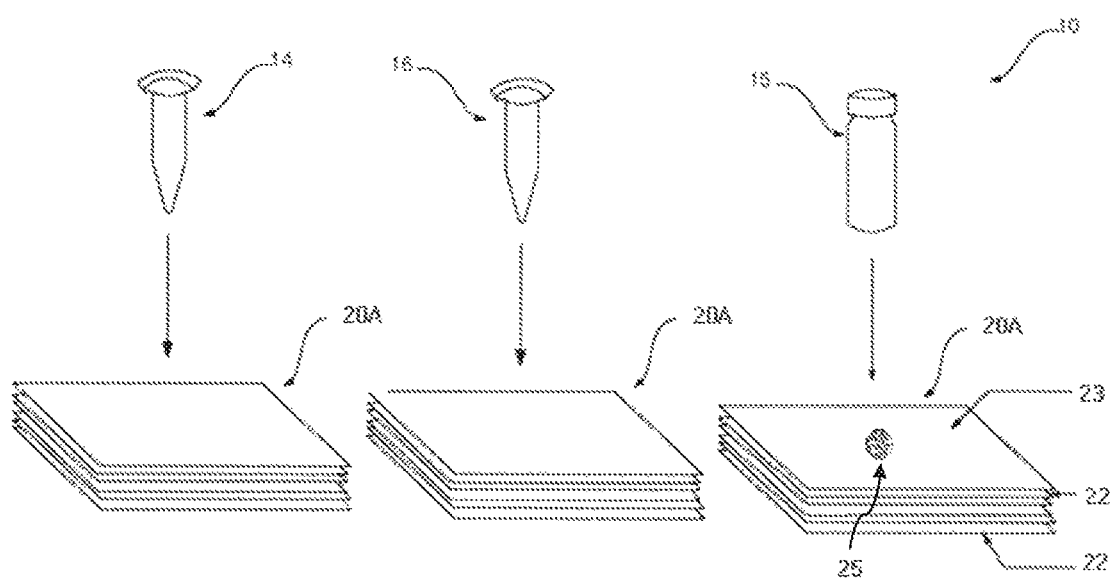
FIG. 3 is a schematic representation of some of the steps comprised in the membrane based assay method for detection of endotoxins in a sample as per Example 5.
Figure 5A:
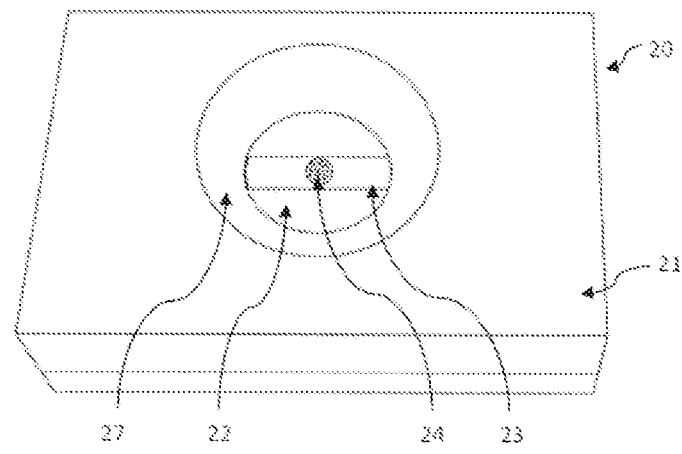
FIGS. 5A and 5B are a schematic representation and a picture, respectively showing detection of endotoxin in sample by the membrane assay method employing conjugates of polymyxin B (PMB) sulfate drug with GNPs as per Example 6.
Figure 5B:
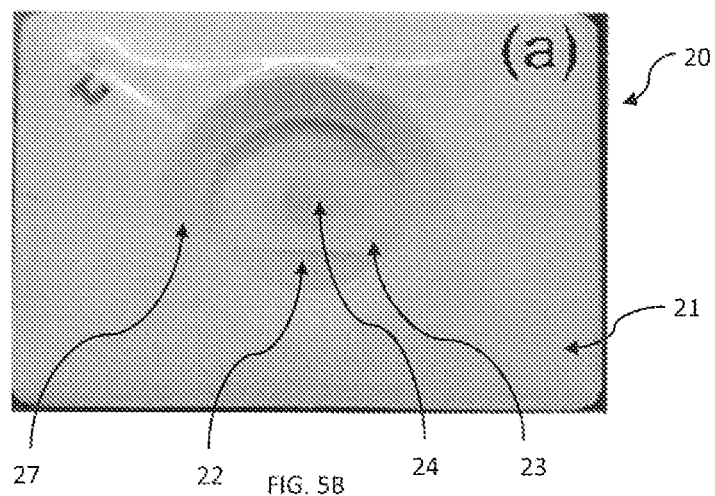

Detection of Endotoxin by Membrane Based Assay Using PMB-GNPs Conjugates:

Schematic representation of some of the steps of a membrane based assay is illustrated in FIG. 3. A 20 µL drop of serum sample 14 containing the target endotoxin was injected over the membrane 20A of the membrane device 20 (not shown in FIG. 3). The quick wicking action of the membrane and that of the absorbent pads below led to the immediate spreading of the drop into a uniform disc shape. After 3 min, 100 µL of 1% w/v bovine serum albumin (BSA) solution 16 was added to the membrane to minimize any non-specific binding in the subsequent steps. Next, 100 µL of 1 nM PMB-conjugated GNP suspension 15 was injected over the membrane over the same place at which the sample and BSA were spotted, within 3 seconds of adding of the PMB-conjugated GNP suspension due to binding of the GNPs with LPS in the sample a pink spot appeared (FIGS. 5A and 5B). The step of addition of PMB-conjugated GNP suspension was repeated until there was no change in the hue of pink spot. A final wash step with 100 µL of ultrapure DI water was included to remove any excess particles. The end results were compared against an indicator score card (FIG. 4) as described in Example 6, within 3 minutes of time window or before the coloured spot faded to determine the endotoxin concentration in the sample. The overall time required for each assay was approximately less than 5 minutes proving that the membrane based assay of the present invention is easy and rapid for detection of endotoxin as compared to the conventionally laboratory based complex methods taking long hours for the detection of endotoxin in the sample.

Example 6

Preparation of an Indicator Chart for Determination of Concentration of Endotoxin in the Sample and Accuracy of the Assay:

To determine how the colour intensity of the spot developed after performing the flow though assay varies with sample endotoxin concentration, known dilutions of endotoxin samples were prepared from a stock solution. Negative control experiments were performed under identical conditions with endotoxin-free serum and pyrogen-free ultrapure DI water. The stock solution was prepared by first reconstituting a known quantity of lyophilized lipopolysaccharide (LPS) powder (Sigma Aldrich) in endotoxin-free water and vigorously vortexing it for 15 min followed by 30 min of sonication. A 5% v/v of this was then added to the serum to obtain a final stock. The carefully calibrated spiked serum samples in the clinically-relevant range of 10 pg/mL to 10 ng/mL were then processed several times using our flow though assay (protocol discussed above) and based on the blind reviewing of the colour intensities developed, a general comprehensive indicator chart was generated as shown in FIG. 4, wherein, "++++" (colour with the darkest tint) indicates >10 ng/mL of endotoxin level, "+++" (colour with one shade lighter than the darkest tint i.e. "++++") indicates 1-10 ng/mL of endotoxin level, "++" (colour with two shades lighter than the darkest tint) indicates 500 pg/mL-1 ng/mL of endotoxin level, "+" (colour with three shades lighter than the darkest tint) indicates 100-500 pg/mL of endotoxin level and "±" indicates <100 pg/mL of endotoxin level. This colour chart was used as an indicator chart (FIG. 4) for quantification of endotoxin levels in the sample. The colour intensity of the spots increased monotonically with increasing concentration of endotoxin in the serum samples. The dynamic range of operation for the membrane based assay was optimized between 100 pg/mL-10 ng/mL to meet the requirements of clinical applications. The lowest limit of detection (LOD) by eye was 10 pg/mL and negative controls gave no significant background signal proving the technique to be specific as desirable.

Example 7

Correlation Between Endotoxin Concentrations Measured in Serum Samples by Membrane Based Assay Using Indicator Chart with that of White Blood Cells (WBC) Count:

Hematological dysfunction is a definite manifestation of sepsis and is seen in all of the patient samples as a host response to infection and to restore homeostasis. Leukocytes, in general WBCs, are useful and affordable markers for infection.

Normal counts of WBCs range between 4500 and 11000 cells/mm$^3$ and, both abnormally high and low counts of WBC are indicators of infection (Manual differential cell counts help predict bacterial infection. A Multivariate Analysis. Wile M J, Homer L D, Gaehler S, Phillips S, Millan J Am J Clin Pathol. 2001 May; 115(5):644-9).

The WBCs were counted in 18 whole blood samples using a 5-Part Haematology Analyser Lab Life D5 Supreme Model, Mindray Medical Inc. following manufacturer's protocol. Serum samples separated from the same 18 whole blood samples as per Example 4 were tested for endotoxin using the membrane device as per Example 1 and following the method as per Example 5. The correlation between endotoxin concentrations measured in serum samples by Reviewers 1 and 2 with the help of colour chart and theft corresponding WBC count are shown in graph in FIG. 8.

Figure 8:
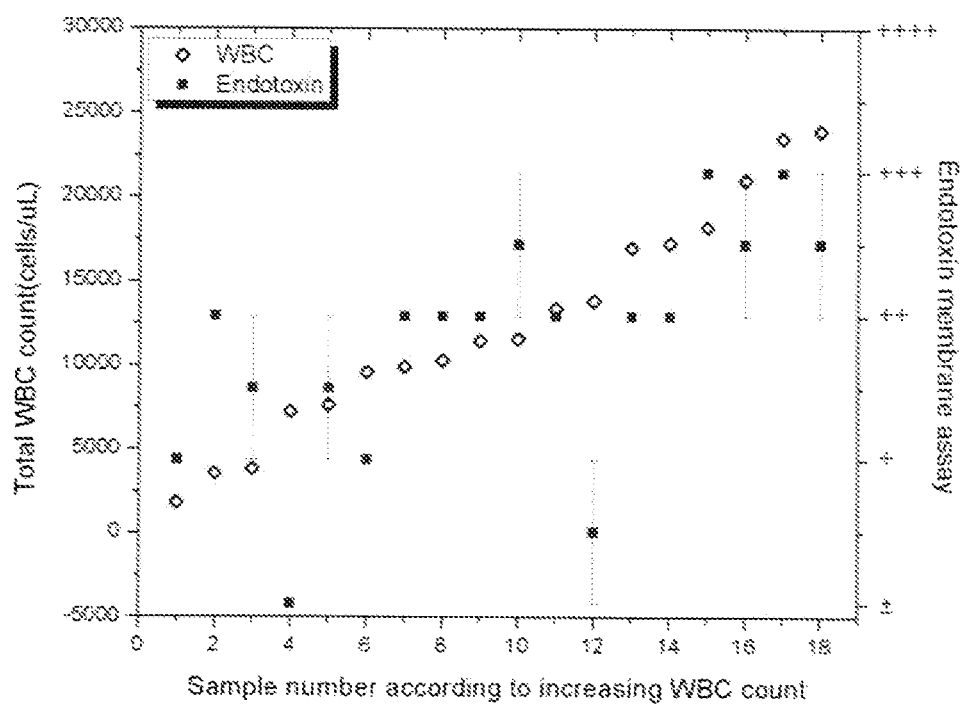
FIG. 8 is a graph showing correlation between the endotoxin levels measured in serum samples by two independent Reviewers (represented by squares) with the help of the colour chart and their corresponding total white blood cell (WBC) counts (represented by diamonds).

Of the 18 samples tested, almost all but four showed good correlation with the WBC counts (FIG. 8). Considering the normal range and physiological variation of WBCs, these deviations between WBC count and serum endotoxins concentration measured using the membrane device of Example 1 seem to be well within clinically acceptable limits. No data is available in the public domain that exemplifies a direct relationship between WBCs and serum endotoxins levels, however, the inventors of the present invention have been able to provide the same with this example.

Example 8

Correlation Between Endotoxin Concentrations Measured in Serum Samples by Membrane Based Assay Using Indicator Chart with that of Neutrophil Count:

Neutrophils are important components of a host's natural defense against pathogens and are produced in large numbers to counter infecting agents. Hence, an increase in their percentage beyond normal levels of ~75% is in a way good correlation to the host response to sepsis. There are situations when a decrease in neutrophil count (<40%) may also be seen in sepsis.

A direct correlation between serum endotoxin concentrations and neutrophil counts has not yet been reported elsewhere, however, the inventors of the present invention have been able to show the correlation with this example.

Neutrophils were counted in 18 whole blood sample using a 5-Part Haematology Analyser Lab Life D5 Supreme Model, Mindray Medical Inc following manufacturer's protocol. The toxic granules in neutrophils were detected in peripheral blood smear under a light microscope with differential staining using standard protocols.

Serum samples separated from the same whole blood samples as per Example 4 were tested for endotoxin using the membrane device as per Example 1 and following the method as per Example 5. The correlation between endotoxin concentrations measured in serum samples by Reviewers 1 and 2 with the help of colour chart and their corresponding neutrophil count are shown in graph in FIG. 9.

Figure 9:
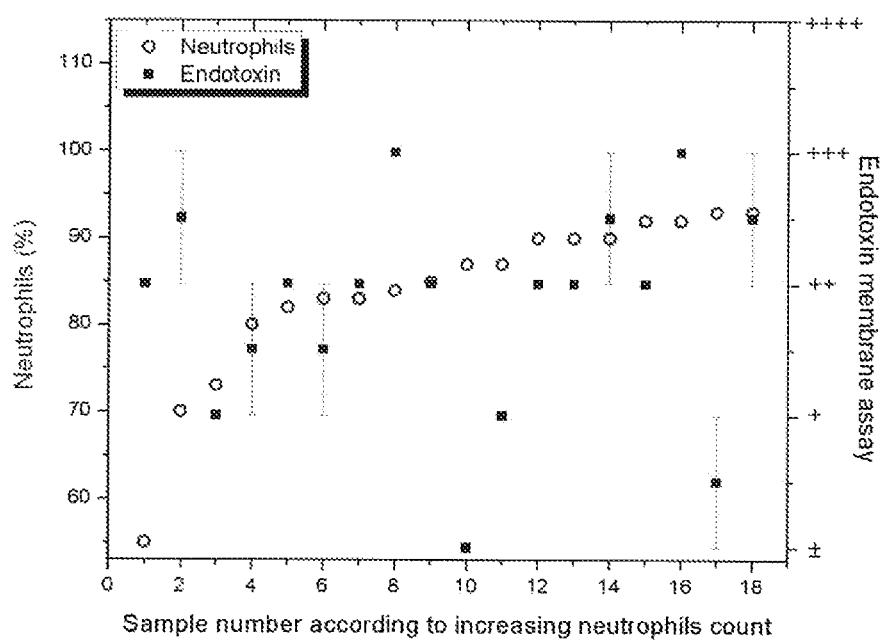
FIG. 9 is a graph showing correlation between endotoxin concentrations measured in serum samples by two independent Reviewers (represented by squares) with the help of the colour chart and their corresponding neutrophil percentage (represented by circles).

Of the 18 samples tested, all of which were toxic granule positive (confirming sepsis), 12 samples showed good correlation between the neutrophil and serum endotoxin levels (FIG. 9). The small deviation may probably be due to the small size of the data set (n=18).

This example illustrates a fairly good correlation between the neutrophil and serum endotoxin levels as measured using the membrane device of Example 1 using the method of Example 5.

Example 9

Preparation of Sushi-GNP Conjugates:

The 34-mer residue sequence of the sushi peptide having following SEQ ID No. 1 with a modified C-terminal for allowing binding to the GNPs via the thiol chemistry was used for conjugating with GNPs.

SEQ ID No. 1: N terminal-HAEHKVKIGVEQKYGQFPQGTEVTYTCSGNYFLM-C terminal

The sushi peptide functionalization was a single step addition process. The sushi peptides (M.W. 4083 Da) were reconstituted in, 40 mM HEPES buffer at pH 7.4 to make a master stock of 0.25 mM. The peptide solutions were then added to 2 nM of GNP suspension in seven different molar ratios, namely 1:1000, 1:2500, 1:5000, 1:7500, 1:10000, 1:15000 and 1:20000 (GNP:sushi peptide), and incubated overnight. The conjugates were stable for all the ratios below 1:10000. So, the suspensions 1:1000 to 1:7500 were used for further processing. These samples were centrifuge washed (4000, 6000 and 8000 rpm for 10 min each) and finally resuspended in the same buffer to give functionalized sushi peptide:GNP conjugates.

Example 10

Figure 6A:
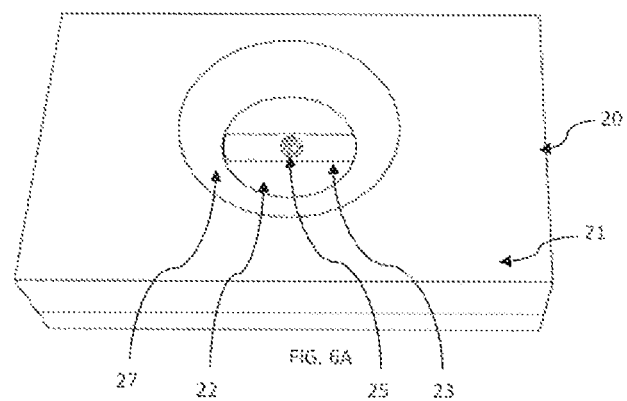
FIGS. 6A and 6B are a schematic representation and a picture, respectively showing detection of endotoxin in a water sample by the membrane assay method employing conjugates of sushi peptide with GNPs as per Example 10.
Figure 6B:
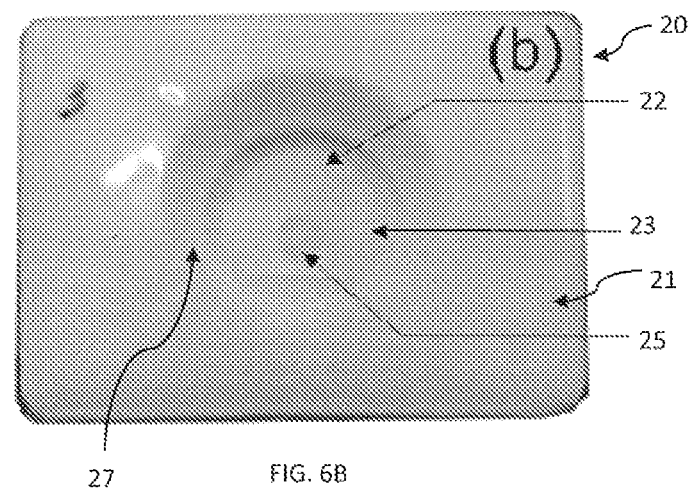
Figure 7A:
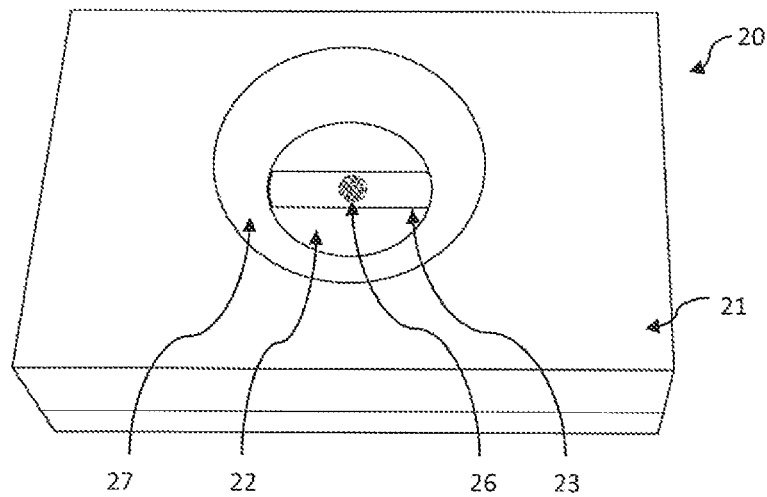
FIGS. 7A and 7B are a schematic representation and a picture respectively showing detection of endotoxin in a serum sample by the membrane assay method employing conjugates of sushi peptide with GNPs as per Example 10.
Figure 7B:
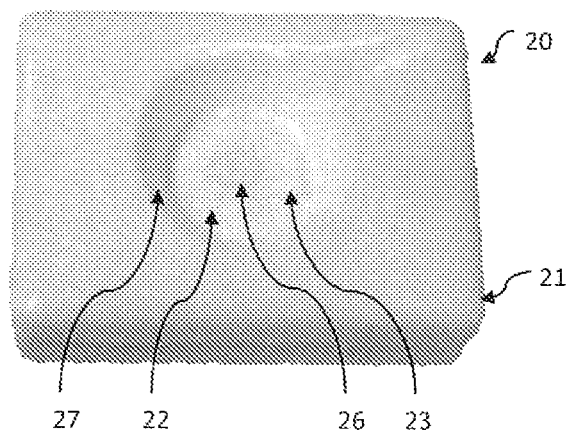

Detection of Endotoxin by Membrane Based Assay Using Sushi Peptide-GNP Conjugates:

Functionalized sushi peptide-GNP conjugates as prepared in Example 9 were used for performing membrane based endotoxin assays as follows:

Membrane based assays were performed with sushi peptide-GNP conjugates for a fixed LPS concentration of 1 ng/mL: (a) in spiked water sample with 1:1000 sushi peptide:GNP ratio and (b) in spiked serum sample with 1:1000 sushi peptide:GNP ratio. Visible reddish spots were observed in both cases, which can be seen as spot 25 in FIGS. 6A-6B (with water sample) and spot 26 in FIGS. 7A-7B (with serum sample). These results illustrates that the sushi peptide functionalized GNPs i.e. sushi peptide conjugated to GNPs work well in detecting endotoxin levels both in water and serum samples.

In the invention being thus described, various modifications of the materials and methods used in the practice of the invention will be readily apparent to one of ordinary skill in the art. Such modifications are considered to be encompassed by the scope of the invention as described in the claims below.

The invention claimed is:

1. A membrane based assay method comprising:
   i) placing a sample suspected of containing an endotoxin on a surface of a membrane having affinity to the endotoxin positioned parallelly to at least one layer of a hydrophilic material and optionally placed in an enclosure for securing therein the at least one layer layer(s) of the hydrophilic material and the membrane having affinity to the endotoxin positioned thereon;
   ii) placing at least once a suspension of conjugates of lipopolysaccharide (LPS)-affinity ligand with gold nanoparticles (GNPs) over the same area as the sample placed, wherein the LPS affinity ligand is sushi 3 peptide having SEQ ID NO: 1; and
   iii) detecting or quantifying the endotoxin in the sample based on the appearance of a colour signal.

2. The assay method as claimed in claim 1, wherein the sample suspected of containing the endotoxin is selected from the group consisting of a water sample, liquid sample, industry sample, pharmaceutical industry and product sample, veterinary industry and product sample, food sample, environmental sample, and biological sample.

3. The assay method as claimed in claim 1, comprising the step of adding a protein solution following the placement of the sample over the membrane having affinity to the endotoxin.

4. The assay method as claimed in claim 1, wherein the suspension of the LPS-affinity ligand with the GNPs is placed more than once until the intensity of the colour signal does not change.

5. The assay method as claimed in claim 1, further comprising adding ultrapure water free of the endotoxin over the colour signal appearing subsequent to the placing of the suspension of conjugates of the LPS-affinity ligand with the GNP.

6. The assay method as claimed in claim 1, further comprising the step of comparing the intensity of the colour signal appeared against an indicator chart to determine the endotoxin concentration in the sample for quantifying the endotoxin in the sample.

7. The assay method as claimed in claim 1, wherein a coloured spot appears within 3 seconds of adding the suspension of conjugates of the LPS-affinity ligand with the GNPs over a sample spot.

8. A kit for detection or quantifying of an endotoxin endotoxins in a sample comprising of:
   i) an LPS-affinity ligand conjugated with gold nanoparticles (GNPs), wherein the LPS affinity ligand is sushi 3 peptide having SEQ ID NO: 1; and
   ii) a membrane device to be adopted for detection of the endotoxin endotoxins in a sample comprising:
      a) a membrane having affinity to the endotoxin:
      b) at least one layer of a hydrophilic material positioned parallelly to the membrane having affinity to the endotoxin; and
      c) an enclosure for securing therein the at least one layer layer(s) of the hydrophilic material and the membrane having affinity to the endotoxin positioned thereon.

9. The kit as claimed in claim 8, further comprising at least one of an indicator chart, protein solution, buffer(s), wash reagent(s), endotoxin-free water or reagent(s), additional device(s), container(s), liquid dispenser bottle(s), injector(s), applicator(s), dropper(s) and an insert with instructions for employing the kit to detect the endotoxin in the sample.

10. The kit as claimed in claim 9, wherein the indicator chart is a concentration calibrated colour chart for easy visualization and marked with scoring for quantifying from >10 ng/mL of an endotoxin level to <100 pg/mL of an endotoxin level in the sample.

11. The kit as claimed in claim 9, wherein the additional device(s) is a device for separating plasma from blood.

12. The kit as claimed in claim 9, wherein the protein solution is of bovine serum albumin.

* * * * *

SEQUENCE LISTING

```
<160> NUMBER OF SEQ ID NOS: 1

<210> SEQ ID NO 1
<211> LENGTH: 34
<212> TYPE: PRT
<213> ORGANISM: Artificial Sequence
<220> FEATURE:
<223> OTHER INFORMATION: Sushi peptide
```

```
<400> SEQUENCE: 1

His Ala Glu His Lys Val Lys Ile Gly Val Glu Gln Lys Tyr Gly Gln
1               5                   10                  15

Phe Pro Gln Gly Thr Glu Val Thr Tyr Thr Cys Ser Gly Asn Tyr Phe
            20                  25                  30

Leu Met
```